United States Patent [19]

Cuenod

[11] Patent Number: 5,733,601
[45] Date of Patent: Mar. 31, 1998

[54] METHOD OF AND ARTICLE FOR APPLYING AGENT TO A SUBSTRATE

[76] Inventor: Ronald P. Cuenod, P.O. Box 770008, Houston, Tex. 77215-0008

[21] Appl. No.: 632,893

[22] Filed: Apr. 16, 1996

[51] Int. Cl.$^6$ .................................................. B05D 5/10
[52] U.S. Cl. .................... 427/208.4; 427/2.31; 427/140; 427/336; 602/8; 206/411
[58] Field of Search ........................... 427/2.31, 340, 427/341, 342, 389.8, 140, 336, 208.4; 428/253, 254, 268; 602/8; 206/411

[56] References Cited

U.S. PATENT DOCUMENTS

| | | | |
|---|---|---|---|
| 4,131,114 | 12/1978 | Kirkpatrick et al. | 427/2.31 X |
| 4,609,578 | 9/1986 | Reed et al. | 428/76 |
| 4,667,661 | 5/1987 | Scholz et al. | 128/90 |
| 5,370,927 | 12/1994 | Scholz et al. | 428/254 |
| 5,540,652 | 7/1996 | Callinan | 427/341 X |
| 5,553,366 | 9/1996 | Novack et al. | 427/2.31 X |

*Primary Examiner*—Michael Lusignan
*Attorney, Agent, or Firm*—Alton W. Payne

[57] ABSTRACT

The present invention relates to gradually applying a slippery agent to resin impregnated cloth for generating a gradient of slippery agent on the cloth whereby the outward most exposed portions of the cloth wound on a pipe have the highest concentration of slippery agent and the concentration of slippery agent decreases with the depth of the cloth wound around the pipe. The method of the present invention comprising the steps of impregnating the cloth with the resin, impregnating the spool with the slippery agent such that the slippery agent is removably engaged with the spool and the slippery agent is uniformly distributed on the spool, receiving the cloth on the spool for generating an assemblage comprising the resin impregnated cloth and the slippery agent impregnated spool such that no mixture of the resin and the slippery agent is effected and the assemblage can be hermetically stored for later use, subsequently activating the resin in the cloth by engaging the assemblage with water, removing the cloth from the spool by receiving the cloth on the pipe, such that the combined effect of activating the resin on the cloth and removing of the cloth from the spool provides that the slippery agent on the spool is gradually applied to the resin impregnated cloth for generating a gradient of slippery agent on the cloth whereby the outward most exposed portions of the cloth received on the pipe have the highest concentration of slippery agent and the concentration of slippery agent decreased with the depth of the cloth wrapped around the pipe. Also, an article of manufacture is provided.

14 Claims, 3 Drawing Sheets

METHOD OF AND ARTICLE FOR APPLYING AGENT TO A SUBSTRATE

FIELD OF THE INVENTION

This invention relates to the application of a slippery agent to a substrate or sheet material coated with a water-activated material, curable polymeric resin, water-activated acrylic or the like. Specifically, the present invention relates to applying the slippery agent to resin impregnated cloth for generating a gradient of slippery agent on the cloth whereby the outward most exposed portions of the cloth wound on a pipe have the highest concentration of slippery agent and the concentration of slippery agent decreases with the depth of the cloth wound around the pipe.

BACKGROUND OF THE INVENTION

Resin-coated materials have been used to brace, buttress, secure and support in various ways. For example, a common use of resin-coated cloth is in making casts for broken bones and other medical situations where support and structure can be individually shaped to the particular situation. Commercially, resin-coated cloth and related substances have been used in many ways. Resin-coated cloth has been used to stop leaks in, for example, plastic or composite pipes, conduit, HVAC delivery and return passages including pipes and hoses, generally, due to cracks, corrosion, joint separation, split piping and other related problems. Resin-coated materials can be used for hose as well as pipe repair to stop leaks to aide in the prevention of corrosion and to reinforce pipe joints. Also, resin-coated material can be used to protect metal surfaces when adapted for use below ground. Still further, such uses may be in association with metal, plastic and fiberglass materials, such as, steel, plastic, fiberglass, copper, aluminum, rubber and PVC materials in air, underground or under water, encasement of lead and asbestos pipes and electrical cables. Uses vary dramatically in various industries, for example, the chemical industry, processing plants, the public service industry, and the commercial marine industry.

Typically, resin-coated products are hand applied in a tape format or by mechanical device or by a combination of hand and mechanical. In a simple case, a roll of tape is "activated" and unrolled by hand around the structure which is to be protected or sealed. Particularly, a urethane coating may be applied to many different substrates. It should be noted by those skilled in the art that any water-activated material, acrylic or polymer is acceptable for use with the present invention. Knitted fiberglass and other knitted or woven materials in the form of a webbing is of particular interest as a substrate material because of the ease of use and flexibility of the webbing. Urethane material can be readily engaged with such webbing substrates to form a readily pliable roll of gauze-like material.

Descriptions of urethane material engaged with a knitted fiberglass webbing substrate are found in U.S. Pat. No. 4,609,578, issued Sep. 2, 1986 to Katherine E. Reed, entitled Resin-Coated Extensible Heat-Set Fiberglass Knit Tape; U.S. Pat. No. 4,667,661, issued May 26, 1987 to Matthew Scholz, et al., entitled Curable Resin-Coated Sheet Having Reduced Tack; and U.S. Pat. No. 4,774,931, issued Oct. 4, 1988 to Matthew T. Scholz, et al., entitled Curable Resin-Coated Sheet Having Reduced Tack which patents are incorporated by reference herein for all purposes. The above noted patents describe various fiberglass tape materials which could be used in practicing the present invention.

Prior known devices have significant draw backs and problems. Particularly, the resin coated cloth or substrate is extremely tacky. The tacky nature of the resins is due to the chemical nature of the resin and the associated curing process of the prepolymer as described in the cited patents. The tackiness makes it extremely difficult to affix the cloth around a pipe or the like because the resin tends to stick to the hands of the applicator or any other device used for application. Particularly, after the roll or rolls are wrapped around the pipe, but before the curing process is complete and hardening has affected, some working of the applied material is necessary. Working the applied material requires a massaging of the material to smooth the surface and to pack the material, by what ever means such as hand, mechanical device or a combination of hand and mechanical. Working the wrapped material enhances the security of the material around the pipe and for preventing any leaks from the pipe. Particularly, the working of the material is typically accomplished by smoothing the material with a gloved hand as the curing process is effected and the material hardens. Thus, molding the tape material around the pipe is difficult because the gloved hands or mechanical device sticks to the resin thereby preventing smoothing. In this situation, the layers of material will pull apart form each other thus requiring reforming of part of the material around the pipe.

It is, therefore, feature of the present invention to provide a method for transferring a slippery agent from a spool to a cloth having a resin such that the outward most exposed portions of the cloth received on a pipe have the highest concentration of slippery agent and the concentration of slippery agent decreases with the depth of the cloth wrapped around the pipe.

Another feature of the present invention is to provide a method whereby the slippery agent and the resin are retained independent and not mixed together prior to the material being affixed to a pipe.

Yet another feature of the present invention is to provide a method whereby the slippery agent is applied to a resin impregnated cloth or substrate simultaneously with wrapping the resin impregnated cloth around a pipe.

Additional features and advantages of the invention will be set forth in part in the description which follows, and in part will become apparent from the description, or may be learned by practice of the invention. The features and advantages of the invention may be realized by means of the combinations and steps particularly pointed out in the appended claims.

SUMMARY OF THE INVENTION

To achieve the foregoing objects, features, and advantages and in accordance with the purpose of the invention as embodied and broadly described herein, a method for transferring a slippery agent from a spool to a cloth having a resin is provided. The slippery agent is required for smoothing the surface of the resin/cloth surface when the tape is applied around a pipe for securing a hole in the pipe. The resin is activated by water to form a wet adhesive and thereafter cures to form a rigid structure. Preferably, the slippery agent is applied in gradually increasing proportions to the length of tape which will ultimately be near the surface and requires to be smoothed. The method comprising the steps of impregnating the cloth with the resin. Impregnating the spool with the slippery agent such that the slippery agent is removably engaged with the spool. Alternately, the slippery agent may be uniformly distributed on the spool. The cloth is received on the spool for generating an assemblage. The assemblage comprises the resin impregnated cloth and the slippery agent impregnated spool such that no mixture of the resin and the slippery agent is effected. The assemblage can be hermetically stored for later use. The assemblage is subsequently engaged with water for activating the resin in the cloth. The cloth is removed from the spool by receiving the cloth on the pipe. The combined effect of activating the resin on the cloth and removing of the cloth from the spool provides that the slippery agent on the spool is gradually applied to the resin impregnated cloth. Gradually applying the slippery agent to the cloth provides for generating a gradient of slippery agent on the cloth. The gradient of slippery agent provides that the outward most exposed portions of the cloth received on the pipe have the highest concentration of slippery agent and the concentration of slippery agent decreases with the depth of the cloth wrapped around the pipe.

Another embodiment of the method of the present invention comprising the steps of coating a cloth with a water-activated material and coating a spool with a slippery agent. The slippery agent is removably engaged with the spool. The cloth is received on the spool for generating an assemblage comprising the cloth covered with the water-activated material and the spool covered with the slippery agent. Mixture of the resin and the slippery agent is inhibited and the assemblage can be hermetically stored for later use. Subsequently the water-activated material in the cloth is activated by engaging the assemblage with water. The cloth is removed from the spool by receiving the cloth on the pipe. The combined effect of activating the water-activated material on the cloth and thereafter removing the cloth from the spool provides that the slippery agent on the spool is applied to the water-activated material coated on the cloth for generating a gradient of slippery agent on the cloth. The slippery agent has a concentration which is a function of the length of the cloth. More particularly, the method may include the step of uniformly coating the spool with the slippery agent. Also, the method may include the concentration as a function of the length of the cloth provides that the outward most exposed portions of the cloth received on the pipe have the highest concentration of the slippery agent and the concentration of the slippery agent is constant over a predetermined length of the cloth wrapped around the pipe. Further, the method may include the concentration as a function of the length of the cloth provides that the outward most exposed portions of the cloth received on the pipe have the highest concentration of slippery agent and the concentration of slippery agent decreases with the depth of the cloth wrapped around the pipe. Still further, the method may include the concentration as a function of the length of the cloth provides that the highest concentration of slippery agent is multi-modal with the depth of the cloth wrapped around the pipe. More particularly, the method associated with the concentration as a function of the length of the cloth being multi-modal provides that the highest concentration of slippery agent is bi-modal with the depth of the cloth wrapped around the pipe.

Another embodiment of the method of the present invention comprises the steps of impregnating a cloth with a resin and a spool with a slippery agent. The slippery agent is removably engaged with the spool and the slippery agent is uniformly distributed on the spool. The cloth is received on the spool for generating an assemblage. The assemblege comprises the resin impregnated cloth and the slippery agent impregnated spool such that no mixture of the resin and the slippery agent is effected and the assemblage can be hermetically stored for later use. The resin is subsequently activated in the cloth by engaging the assemblage with water. The cloth is removed from the spool by receiving the cloth on the pipe such that the combined effect of activating the water-activated material on the cloth and thereafter removing the cloth from the spool provides that the slippery agent on the spool is applied to the water-activated material coated on the cloth for generating a gradient of slippery agent on the cloth whereby the slippery agent has a concentration which is a function of the length of the cloth. The method may comprises the step of uniformly coating the spool with the slippery agent. Also, the method may include the concentration as a function of the length of the cloth provides that the outward most exposed portions of the cloth received on the pipe have the highest concentration of the slippery agent and the concentration of the slippery agent is constant over a predetermined length of the cloth wrapped around the pipe. Further, the method may include the concentration as a function of the length of the cloth provides that the outward most exposed portions of the cloth received on the pipe have the highest concentration of slippery agent and the concentration of slippery agent decreases with the depth of the cloth wrapped around the pipe. Still further, the method may include the concentration as a function of the length of the cloth provides that the highest concentration of slippery agent is multi-modal with the depth of the cloth wrapped around the pipe. More particularly, the method associated with the concentration as a function of the length of the cloth being multi-modal provides that the highest concentration of slippery agent is bi-modal with the depth of the cloth wrapped around the pipe.

The methods for transferring a slippery agent from a spool to a cloth having a water-activated material may include coating the cloth with a polymer.

In yet another embodiment of the present invention an article of manufacture is provided for securing a pipe. The article comprises a cloth, a water-activated material, a spool and a slippery agent. The water-activated material is coated on the cloth. The water-activated material, when activated, forms a wet adhesive and thereafter cures to form a rigid structure. The slippery agent is removably engaged with the spool. An assemblage is formed comprising the cloth covered with the water-activated material and the spool covered with the slippery agent. The assemblage provides that no mixture of the resin and the slippery agent is effected until after activation. The assemblage can be hermetically stored for later use. The water-activated material in the cloth is activated by engaging the assemblage with water. The cloth is removed from the spool by receiving the cloth on the pipe. The combined effect of activating the water-activated material on the cloth and thereafter removing the cloth from the spool provides that the slippery agent on the spool is applied to the water-activated material coated on the cloth for generating a gradient of slippery agent on the cloth. The slippery agent has a concentration which is a function of the length of the cloth.

BRIEF DESCRIPTION OF THE DRAWINGS

The accompanying drawings which are incorporated in and constitute a part of the specification, illustrate a preferred embodiment of the invention and together with the general description of the invention given above and the detailed description of the preferred embodiment given below, serve to explain the principles of the invention.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENTS

Reference will now be made in detail to the present preferred embodiments of the invention as described in the accompanying drawings.

Figure 1:
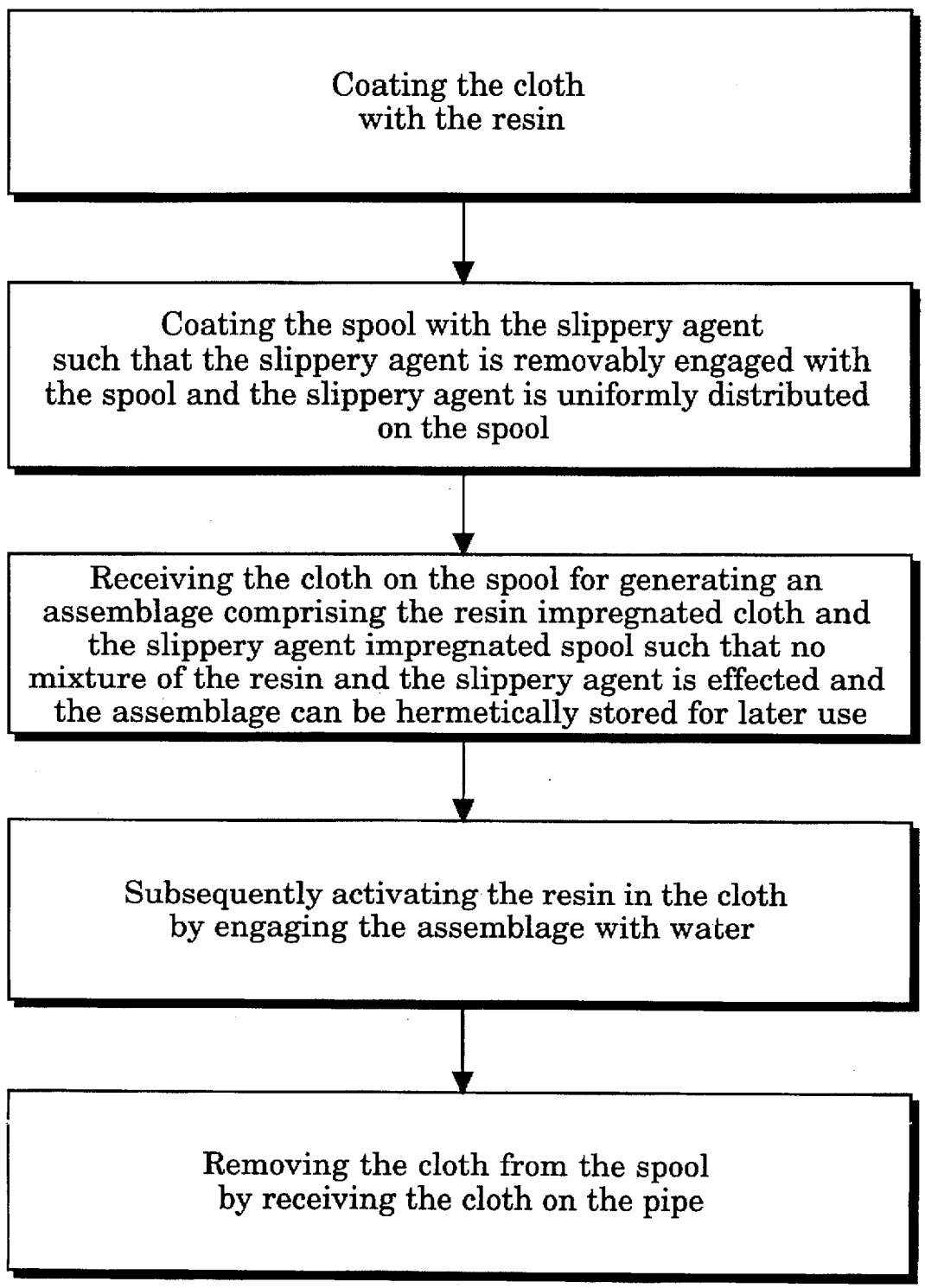
FIG. 1 is a flow chart illustrating a preferred embodiment of the present invention.

FIG. 1 is a flow chart illustrating a preferred embodiment of the present invention. FIG. 1 illustrates the method of transferring a slippery agent from a spool to a cloth having a resin. The slippery agent is required to be affixed to the resin for smoothing the resin impregnated cloth after the tape is wrapped around a pipe. The present invention is especially adaptable when the tape is provided for securing a hole in the pipe. Typically, the resin is activated by water to form a wet adhesive which cures to form a rigid structure. The method comprises the steps of impregnating the cloth with the resin and impregnating the spool with the slippery agent. The slippery agent is removably adhered to the spool so that it can be removed from the spool. Preferably, the slippery agent is uniformly distributed on the spool, but the distribution requirements are use dependent. The cloth is received on the spool for generating an assemblage. The assemblage comprises the resin impregnated cloth and the slippery agent impregnated spool. The assemblage is provided such that no mixture of the resin and the slippery agent is effected and the assemblage can be hermetically stored for later use. Subsequently, the resin in the cloth is activated by engaging the assemblage with water. The cloth is removed from the spool by receiving the cloth around the pipe. The combined effect of activating the resin on the cloth and removing the cloth from the spool provides that the slippery agent on the spool is gradually applied to the resin impregnated cloth. The combined effect generates a gradient of slippery agent on the cloth. The, the outward most exposed portions of the cloth received on the pipe have the highest concentration of slippery agent, and the concentration of slippery agent decreases with the depth of the cloth wrapped around the pipe.

The spool can be comprised of many types of materials. For example, the spool can be felt or it can be a rigid porous material such as sintered material, absorbent plastic or the like. Further, the spool could be a cloth material or even a hard plastic material with knobby-type protrusions.

Figure 2:
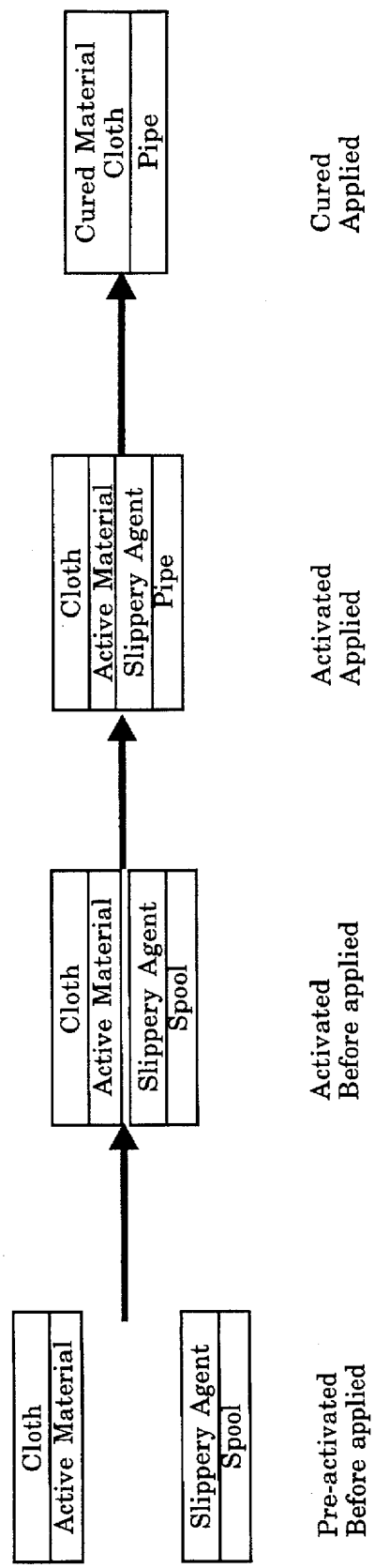
FIG. 2 is a schematic view of a preferred embodiment of an article of the present invention.

FIG. 2 is a schematic view of a preferred embodiment of the apparatus of the present invention. The apparatus of the present invention provides that the slippery agent and the resin are not mixed prior to the time the material is wrapped around the pipe.

Figure 3:
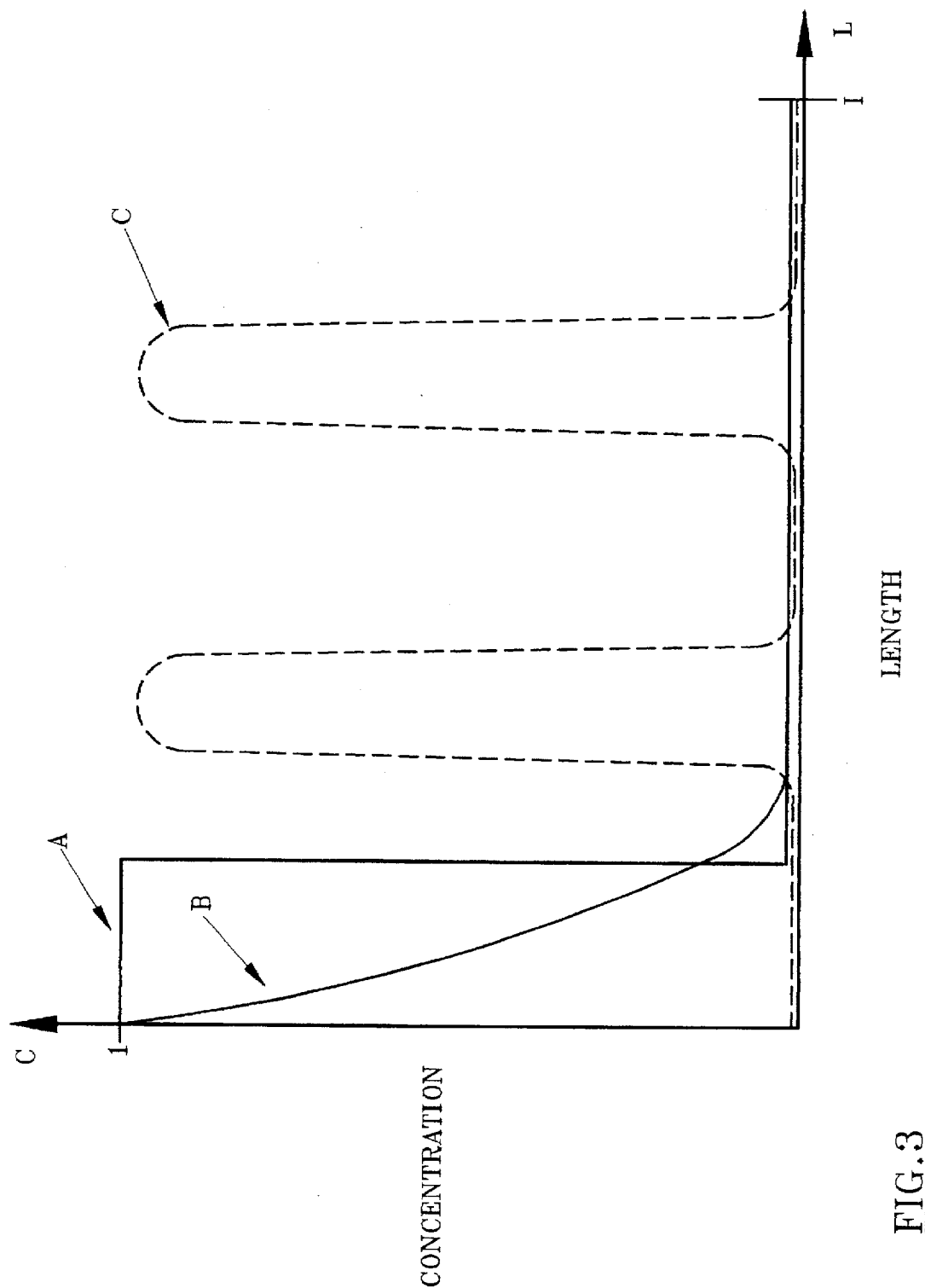
FIG. 3 is a graph of concentration versus tape length/depth for several applications of the present invention.

FIG. 3 is a graph of concentration verses tape length or depth for several applications of the present invention. Curve A illustrates the present invention used with a linear gradient such that the deposition of slippery agent to the cloth has a linear function. When it is desirable for the slippery agent to be more dominant on the surface, more slippery agent must be applied at the inner most portion of the cloth on the spool which corresponds to the outer most portion around the receiving pipe. In FIG. 3, curve B is representative of the situation where the gradient of the slippery agent on the cloth is non-linear with the higher concentrations at the outward extremities of the cloth as it is wrapped around the pipe. In such situations, increased amounts of slippery agent may be required due to various conditions, for example, high ambient temperatures.

In other situations, the working of the material around the pipe may be better served by more slippery agent being at a greater depth within the cloth wrapped around the pipe. In FIG. 3, curve C illustrates the non-linear deposition gradient of the slippery agent on the cloth such that the slippery agent has greater concentrations at depths within the cloth. More particularly, curve C illustrates a bi-modal concentration distribution of slippery agent along the surface of the cloth. It can be appreciated by those skilled in the art that various functions of concentration with respect to length of cloth are possible and desired for particular needs.

Additional advantages and modification will readily occur to those skilled in the art. The invention in its broader aspects is therefore not limited to the specific details, representative apparatus, and the illustrative examples shown and described herein. Accordingly, the departures may be made from the details without departing from the spirit or scope of the disclosed general inventive concept.

What is claimed is:

1. A method for transferring a slippery agent from a spool to a cloth having a water-activated material, the water-activated material and the slippery agent required for smoothing the surface of the material/cloth surface when the tape is applied around a pipe for securing a hole in the pipe, which water-activated material forms a wet adhesive when activated and thereafter cures to form a rigid structure such that the concentration of the slippery agent is applied as a function of the length of the tape which slippery agent will ultimately be near the outer surface of the pipe which requires to be smoothed, the method comprising the steps of:

(a) coating the cloth with the water-activated material,
   (b) coating the spool with the slippery agent such that the slippery agent is removably engaged with the spool,
   (c) receiving the cloth on the spool for generating an assemblage comprising the cloth covered with the water-activated material and the spool covered with the slippery agent such that no mixture of the resin and the slippery agent is effected and the assemblage can be hermetically stored for later use,
   (d) subsequently activating the water-activated material in the cloth by engaging the assemblage with water,
   (e) removing the cloth from the spool by receiving the cloth on the pipe,
   such that the combined effect of activating the water-activated material on the cloth and thereafter removing the cloth from the spool provides that the slippery agent on the spool is applied to the water-activated material coated on the cloth for generating a gradient of slippery agent on the cloth whereby the slippery agent has a concentration which is a function of the length of the cloth.

2. A method for transferring a slippery agent from a spool to a cloth having a water-activated material as defined in claim 1 further comprises the step of uniformly coating the spool with the slippery agent.

3. A method for transferring a slippery agent from a spool to a cloth having a water-activated material as defined in claim 1 wherein the concentration as a function of the length of the cloth provides that the outward most exposed portions of the cloth received on the pipe have the highest concentration of the slippery agent and the concentration of the slippery agent is constant over a predetermined length of the cloth wrapped around the pipe.

4. A method for transferring a slippery agent from a spool to a cloth having a water-activated material as defined in claim 1 wherein the concentration as a function of the length of the cloth provides that the outward most exposed portions of the cloth received on the pipe have the highest concentration of slippery agent and the concentration of slippery agent decreases with the depth of the cloth wrapped around the pipe.

5. A method for transferring a slippery agent from a spool to a cloth having a water-activated material as defined in claim 1 wherein the concentration as a function of the length of the cloth provides that the highest concentration of slippery agent is multi-modal with the depth of the cloth wrapped around the pipe.

6. A method for transferring a slippery agent from a spool to a cloth having a water-activated material as defined in claim 5 wherein the concentration as a function of the length of the cloth provides that the highest concentration of slippery agent is bi-modal with the depth of the cloth wrapped around the pipe.

7. A method for transferring a slippery agent from a spool to a cloth having a resin, the resin and the slippery agent required for smoothing the surface of the resin/cloth surface when the tape is applied around a pipe for securing a hole in the pipe, which resin is activated by water to form a wet adhesive and thereafter cures to form a rigid structure such that the slippery agent is applied in gradually increasing proportions to the length of tape which will ultimately be near the surface which requires to be smoothed, the method comprising the steps of:

(a) impregnating the cloth with the resin, (b) impregnating the spool with the slippery agent such that the slippery agent is removably engaged with the spool and the slippery agent is uniformly distributed on the spool, (c) receiving the cloth on the spool for generating an assemblage comprising the resin impregnated cloth and the slippery agent impregnated spool such that no mixture of the resin and the slippery agent is effected and the assemblage can be hermetically stored for later use, (d) subsequently activating the resin in the cloth by engaging the assemblage with water, (e) removing the cloth from the spool by receiving the cloth on the pipe, such that the combined effect of activating the water-activated material on the cloth and thereafter removing the cloth from the spool provides that the slippery agent on the spool is applied to the water-activated material coated on the cloth for generating a gradient of slippery agent on the cloth whereby the slippery agent has a concentration which is a function of the length of the cloth.

8. A method for transferring a slippery agent from a spool to a cloth having a water-activated material as defined in claim 7 further comprises the step of uniformly coating the spool with the slippery agent.

9. A method for transferring a slippery agent from a spool to a cloth having a water-activated material as defined in claim 7 wherein the concentration as a function of the length of the cloth provides that the outward most exposed portions of the cloth received on the pipe have the highest concentration of the slippery agent and the concentration of the slippery agent is constant over a predetermined length of the cloth wrapped around the pipe.

10. A method for transferring a slippery agent from a spool to a cloth having a water-activated material as defined in claim 7 wherein the concentration as a function of the length of the cloth provides that the outward most exposed portions of the cloth received on the pipe have the highest concentration of slippery agent and the concentration of slippery agent decreases with the depth of the cloth wrapped around the pipe.

11. A method for transferring a slippery agent from a spool to a cloth having a water-activated material as defined in claim 7 wherein the concentration as a function of the length of the cloth provides that the highest concentration of slippery agent is multi-modal with the depth of the cloth wrapped around the pipe.

12. A method for transferring a slippery agent from a spool to a cloth having a water-activated material as defined in claim 11 wherein the concentration as a function of the length of the cloth provides that the highest concentration of slippery agent is bi-modal with the depth of the cloth wrapped around the pipe.

13. A method for transferring a slippery agent from a spool to a cloth having a water-activated material as defined in claim 7 wherein the step of impregnating the cloth with the resin comprises the step of coating the cloth with a polymer.

14. An article of manufacture for securing a pipe comprising:

(a) a cloth, (b) a water-activated material coated on the cloth which water-activated material, when activated, forms a wet adhesive and thereafter cures to form a rigid structure, (c) a spool, (d) a slippery agent removably engaged with the spool, (e) an assemblage comprising the cloth covered with the water-activated material and the spool covered with the slippery agent such that no mixture of the resin and the slippery agent is effected and the assemblage can be hermetically stored for later use, such that the water-activated material in the cloth is activated by engaging the assemblage with water, the cloth is removed from the spool by receiving the cloth on the pipe, such that the combined effect of activating the water-activated material on the cloth and thereafter removing the cloth from the spool provides that the slippery agent on the spool is applied to the water-activated material coated on the cloth for generating a gradient of slippery agent on the cloth whereby the slippery agent has a concentration which is a function of the length of the cloth.

* * * * *